(12) United States Patent
Johnson et al.

(10) Patent No.: US 7,382,458 B2
(45) Date of Patent: Jun. 3, 2008

(54) FIBER OPTIC FLUID PROBE

(75) Inventors: Anthony F. Johnson, St. Louis, MO (US); Michael J. Ponstingl, St. Louis, MO (US)

(73) Assignee: Custom Sample Systems, Inc., Fenton, MO (US)

(*) Notice: Subject to any disclaimer, the term of this patent is extended or adjusted under 35 U.S.C. 154(b) by 490 days.

(21) Appl. No.: 10/815,295

(22) Filed: Apr. 1, 2004

(65) Prior Publication Data

US 2005/0219541 A1 Oct. 6, 2005

(51) Int. Cl.
*G01N 21/00* (2006.01)

(52) U.S. Cl. .................. 356/436; 356/136; 422/82.06

(58) Field of Classification Search ........... 356/436, 356/133, 134, 135, 136
See application file for complete search history.

(56) References Cited

U.S. PATENT DOCUMENTS

| | | | | |
|---|---|---|---|---|
| 4,637,730 A | | 1/1987 | Ponstingl et al. | |
| 4,778,270 A | * | 10/1988 | Kinney et al. | 356/43 |
| 4,826,313 A | * | 5/1989 | Schar et al. | 356/51 |
| 4,829,186 A | * | 5/1989 | McLachlan et al. | 250/373 |
| 4,909,588 A | * | 3/1990 | Harner et al. | 385/12 |
| 4,998,022 A | * | 3/1991 | Tregay | 250/577 |
| 5,241,368 A | | 8/1993 | Ponstingl et al. | |
| 5,399,876 A | * | 3/1995 | LaClair | 250/577 |
| 5,408,313 A | | 4/1995 | Ponstingl et al. | |
| 5,440,126 A | * | 8/1995 | Kemsley | 250/339.12 |
| 5,703,366 A | * | 12/1997 | Sting et al. | 250/341.2 |
| 5,956,132 A | * | 9/1999 | Donzier | 356/133 |
| 6,043,895 A | | 3/2000 | Masterson et al. | |
| 6,118,520 A | * | 9/2000 | Harner | 356/73 |
| 6,363,784 B1 | * | 4/2002 | Gregory | 73/293 |
| 6,535,283 B1 | * | 3/2003 | Heffels et al. | 356/300 |
| 6,567,173 B1 | * | 5/2003 | Johannesen | 356/480 |
| 7,030,976 B2 | * | 4/2006 | Hosseinioun et al. | 356/135 |
| 2004/0201835 A1 | * | 10/2004 | Coates et al. | 356/73 |

* cited by examiner

*Primary Examiner*—Roy M Punnoose
(74) *Attorney, Agent, or Firm*—Thompson Coburn LLP

(57) ABSTRACT

A fiber optic fluid probe is employed in determining characteristics of a fluid or solid dispersed in the fluid into which the probe is immersed. The probe transmits electromagnetic radiation from a source by way of one or more fiber optic fibers and into the fluid, and then senses how the electromagnetic radiation interacts with the fluid. The optical signal returned from the probe, by way of fiber optic cables, is interrogated by an electronic instrument, which correlates the optical response to fluid properties and/or characteristics.

31 Claims, 9 Drawing Sheets

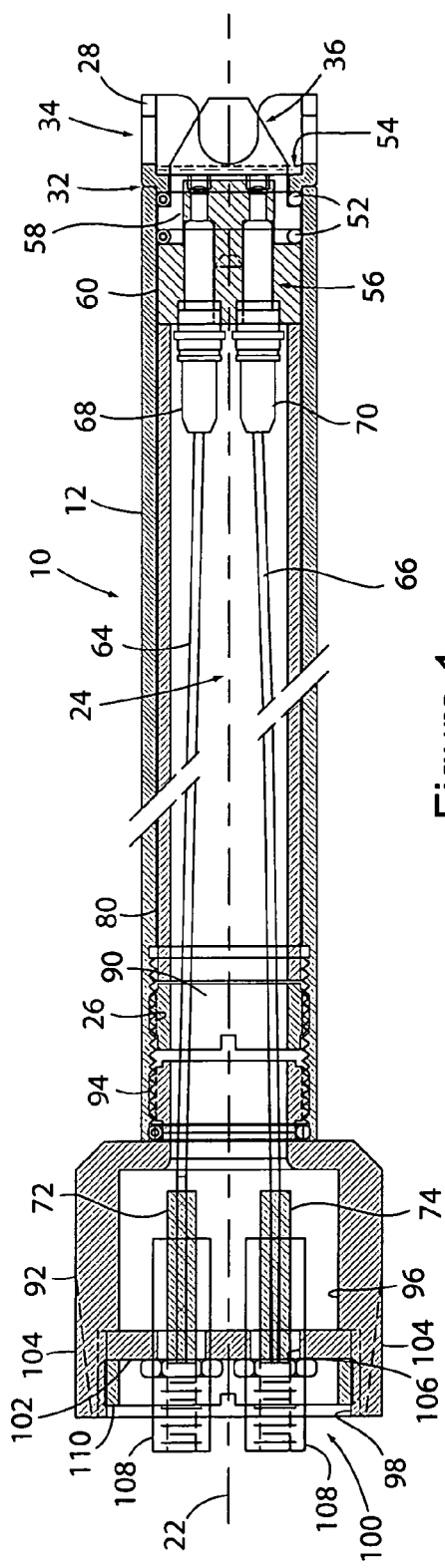
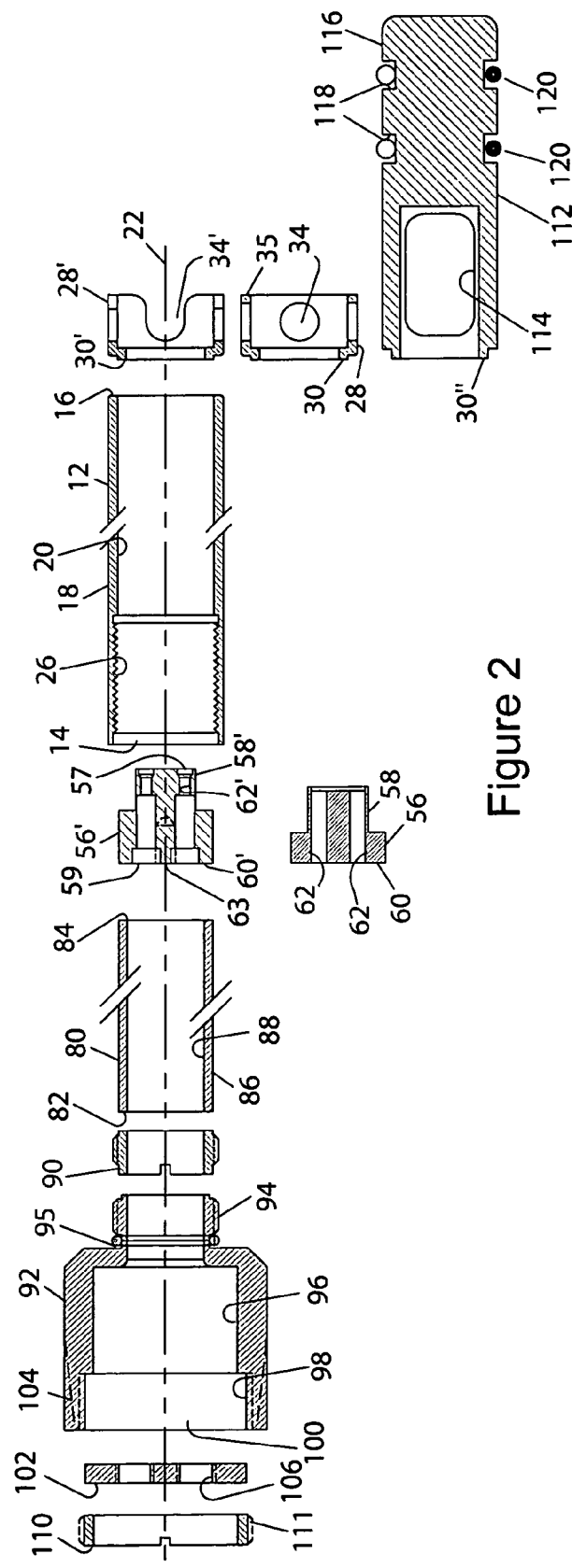
Figure 1
Figure 2

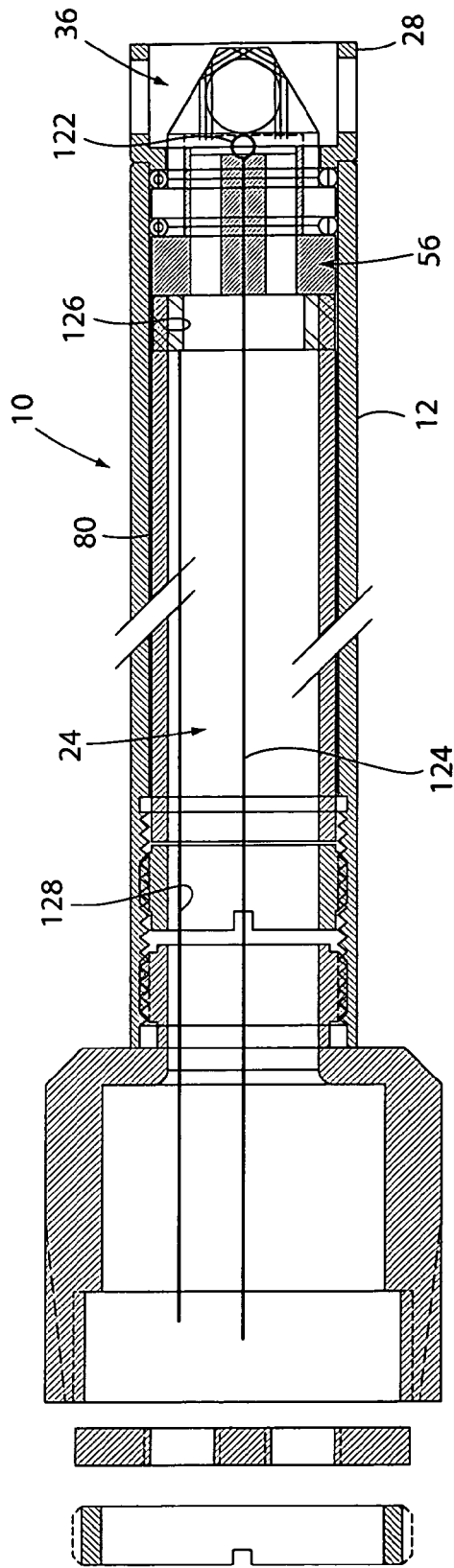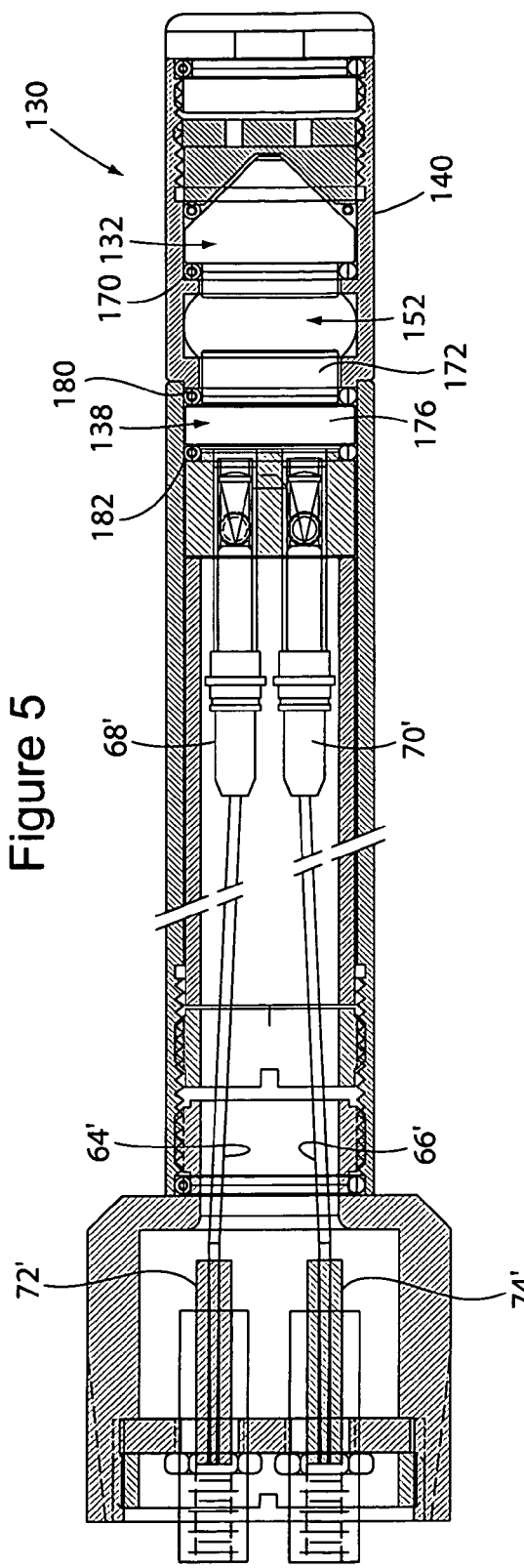
Figure 5
Figure 6a

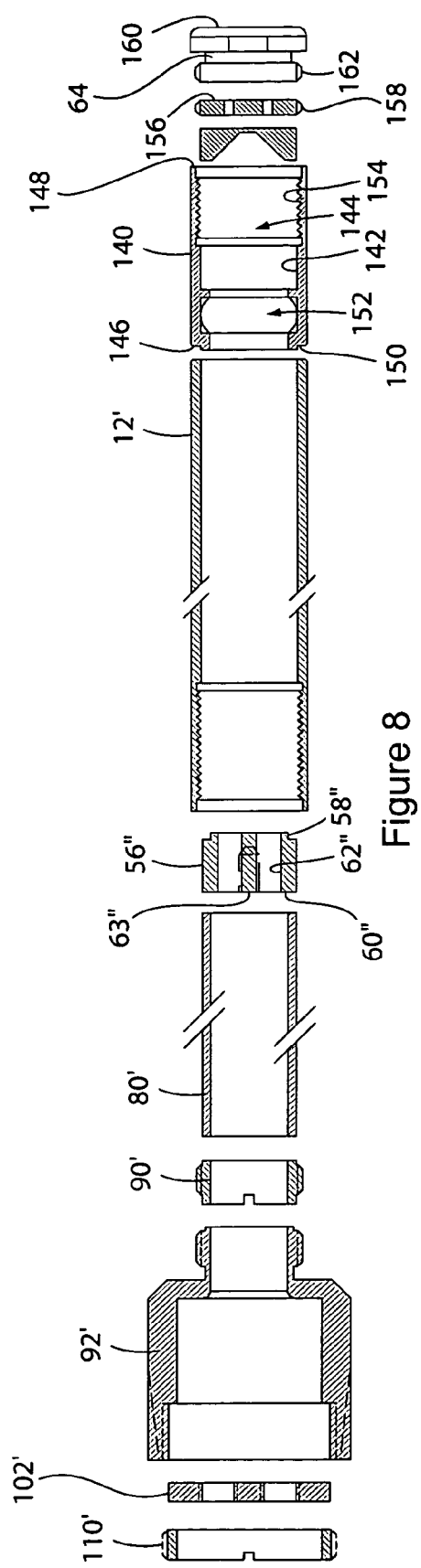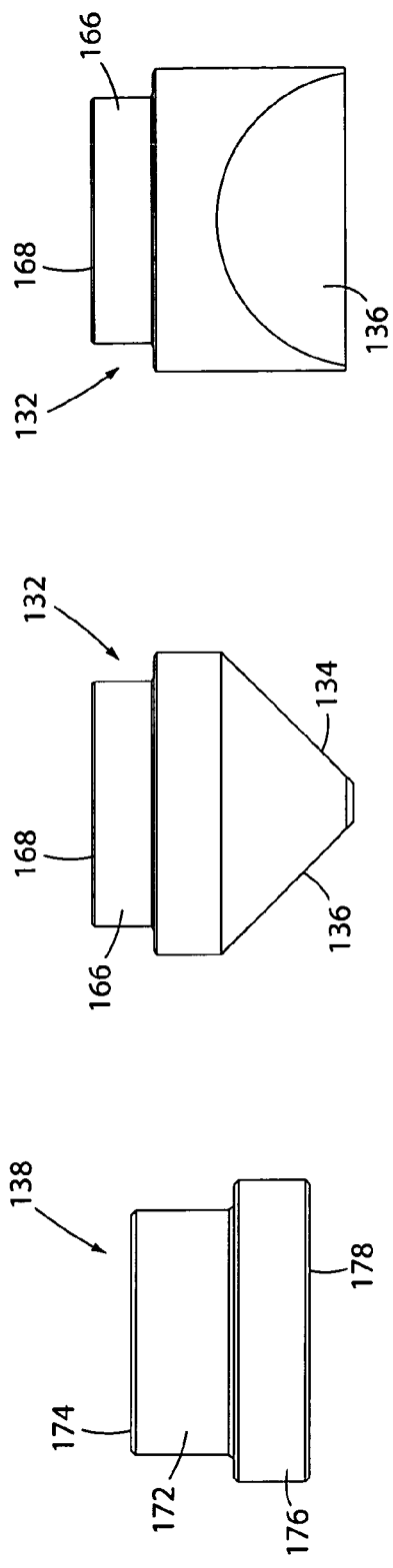

FIBER OPTIC FLUID PROBE

BACKGROUND OF THE INVENTION (1) Field of the Invention

The present invention pertains to a probe that is employed in determining characteristics of a fluid or objects dispersed in the fluid into which the probe is immersed. More specifically, the present invention pertains to a fiber optic probe that transmits electromagnetic radiation typically but not limited to the 200-2200 nanometer region, by way of one or more optic fibers into a fluid, and then senses how the electromagnetic radiation transmitted into the fluid is affected by the fluid or objects in the fluid. By sensing how the transmitted electromagnetic radiation is affected by the fluid, the fiber optic probe enables the determination of certain characteristics and/or properties of the fluid or objects in the fluid.

(2) Description of the Related Art

In the many different types of industrial facilities that process fluids such as chemical processing facilities or chemical laboratories, petroleum processing facilities, waste water treatment facilities, pharmaceutical processing facilities, etc., it is often desirable to monitor or test the characteristics or properties of the fluids being processed in order to regulate or control the processing of the fluids. For example, in facilities that treat waste water to purify the water, it is desirable to monitor the amounts of chemicals added to the waste water during the purification process in order to ensure that a sufficient amount of the chemicals are added to the waste water to result in its purification, and also to ensure that an excessive amount of the purification chemicals are not added to the waste water which would result in needless expense and potential contamination of the water.

In prior art fluid processing facilities, the fluids being processed were often monitored by extracting samples of the fluids or using non-optical based sensors. The samples were then tested to determine the characteristics or properties of the fluids, and thereby evaluate the processing of the fluids. The sampling would require one or more people at the processing facility to physically extract samples of the fluids for analysis. Thus, extracting the samples and then testing the samples would require significant amounts of time during which the fluid processing is continued. If the fluid testing determined that adjustments or changes to the processing were needed, a potentially critical delay would occur before the adjustments would be made. In addition, these testing procedures were at times very hazardous to the human tester, especially where the fluids being processed were potentially corrosive, toxic or explosive liquids or gases.

What is needed to overcome the disadvantages of prior art methods of monitoring industrial fluid processing facilities is an apparatus that continuously monitors the characteristics or properties of a fluid in an industrial fluid processing facility, and provides continuous data on the properties of the fluid which would enable real time adjustments in the processing of the fluid to obtain the desired results.

SUMMARY OF THE INVENTION

The present invention provides several embodiments of fiber optic probes used in monitoring a fluid or solids dispersed in the fluid. The present invention employs fiber optic probes that transmit electromagnetic radiation into a fluid and sense the interaction of the electromagnetic radiation with the fluid or solids suspended in the fluid to enable the determination of properties and characteristics of the fluid or solid in the fluid from the optical response. The fiber optic probes of the invention have novel constructions that employ several of the same component parts in three different types of fiber optic probes. The probes described herein fall into three categories: interaction of the evanescent wave with the fluid or solids dispersed in the fluid using the attenuated total reflection (ATR) method, determination of the transmission of the fluid, and detection of molecular fluorescence from the fluid. All three probes are immersed in the process fluid for in-situ monitoring.

The probe constructions enable slight modifications of the probes to adapt them for use in various different types of environments, and to adapt them for use in performing various different types of optic measurements. The ability to use many of the same component parts in constructing the three different types of fiber optic probes reduces manufacturing costs.

A first embodiment of the fiber optic probe senses the affect of the tested fluid on evanescent wave or alterations in the optical sensing element total internal reflection. This first probe embodiment is an attenuated total reflectance (ATR) probe. The probe has an elongate, hollow tubular body with opposite proximal and distal ends. One of several different types of protective caps is secured to the body distal end.

An optic sensing element, for example a sapphire crystal, is positioned at the probe distal end inside a protective tip guard. Typically the optical sensing crystal has a frustum shape, which results in an ATR element with three sensing surfaces. A proximal end portion of the crystal has a "top hat" like shape, which is received inside the hollow interior of the probe body. A resilient seal, for example a pair of o-ring seals, are positioned around the crystal "top hat" portion. The resilient o-rings provide a seal between the crystal and the interior of the probe body.

A cylindrical optical assembly is positioned adjacent to the probe crystal. The optical assembly holds the distal ends of a pair of fiber optic cables adjacent to the proximal end of the probe crystal. The fiber optic cables extend from the distal end of the probe body, through the hollow interior of the probe body, to the proximal end of the probe body. In variant embodiments of the probe, the optical assembly may also incorporate a thermal sensor for monitoring fluid temperature. In addition, a strain gauge may be positioned adjacent the optical assembly for sensing the pressure of the fluid.

An internal spacing and compression tube is inserted through the interior of the probe body and abuts against the fiber optic support. A compression ring is screw-threaded into the body proximal end, pushing the spacing tube toward the fiber optic support and the optic crystal, and compressing the resilient seals contacting the optic sensing element. The compression of the resilient seals establishes a seal between the probe exterior environment (the process fluid) and the probe interior at the distal end of the probe.

A connector collar is attached to the probe proximal end with the fiber optic cables passing through the connector collar. The proximal ends of the probe fiber optic cables are supported in a positioning plate secured in the interior of the connector collar. The connector collar is adapted for mechanically joining the probe fiber optic cables to lengths of additional fiber optic cables that communicate optical signal from the probe to the testing equipment of the fluid testing facility or lab. The testing equipment determines the characteristics or properties of the tested fluid based on the optical response from the probe.

In use of the attenuated total reflectance probe in testing a fluid in which the probe distal end is immersed, electromagnetic radiation is transmitted through one of the fiber optic cables of the probe to the optical sensing crystal. The electromagnetic radiation is reflected off the internal surfaces of the crystal. The characteristics or a property of the fluid or solids dispersed in the fluid in which the probe crystal is immersed affects either evanescent wave or the total internal reflectance of the crystal. The electromagnetic radiation passing through the optical sensing crystal is directed to the other of the fiber optic cable mounted in the optical assembly, which transmits the optical signal from the probe distal end to the additional fiber optic cables that communicate the optical signal from the probe to the testing equipment. The testing equipment uses the optical response to determine the characteristics and/or properties of the tested fluid or solids dispersed in the fluid.

The second embodiment of the fiber optic probe is called a transmission probe. This probe embodiment employs the same tubular body, fiber optic cables, internal spacing tube, compression ring, fiber positioning plate, and connector collar as described for the ATR probe. The internal optical assembly is modified to function in conjunction with a "top hat" optical sensing window. In the transmission probe, the optical crystal of the ATR probe is replaced by a retro reflection assembly, typically an optical crystal having two metalized reflective surfaces, and by an optical window with a fluid testing chamber in the probe body between the retro reflection assembly and the optical window.

The transmission probe utilizes a measurement specific fluid testing chamber located at the distal end of the tubular body between the optical window and the retro reflection assembly. The fluid testing chamber has a hollow interior. A pair of openings through diametrically opposite sides of the probe body allows the fluid to enter the chamber while the distance between the two optical elements defines the path length of the fluid testing chamber.

The retro reflection assembly is positioned inside the distal end of the probe body. In a typical configuration, the retro reflection assembly is a single integrated unit, with a "top hat" cylindrical trapezoidal shape. The angled surfaces are metalized and the "top-hat" portion contacts the process fluid. A resilient seal, for example an o-ring seal, extends around the "top hat" portion of the optical crystal and seals the crystal inside the probe body.

The optical window is secured inside the probe body on the opposite side of the fluid testing chamber in relation to the retro reflection assembly. The optical window has optically flat opposite distal and proximal end parallel surfaces. A pair of resilient seals extends around the periphery of the optical window adjacent the distal and proximal end surfaces and seals the optical window in the interior of the tubular body.

A modified optical assembly of the previously described embodiment is also employed in the transmission probe. The optical assembly is located in the probe interior and is positioned adjacent the proximal surface of the optical window. As in the previously described embodiment, the optical assembly could also incorporate a thermocouple for sensing the temperature of the process fluid, and/or a strain gauge for sensing the pressure of the process fluid.

The internal spacing and compression tube of the previously described ATR probe embodiment is also employed in the transmission probe. The spacing tube is inserted through the interior of the transmission probe body and abuts against the optical assembly. A compression ring, also used in the previously described probe embodiment, is screw-threaded into the tubular body proximal end and pushes the spacing tube toward the optical assembly and the optical window. The spacing tube compresses the resilient seals that extend around the optical window, sealing the optic window in the interior of the tubular body.

As in the previously described embodiment, the optical assembly receives and supports the distal ends of a pair of fiber optic cables in the probe interior adjacent to the proximal surface of the optical window. The lengths of the fiber optic cables extend through the probe interior to the proximal end of the probe.

A connector collar is attached to the probe body proximal end, as in the previously described embodiment. The proximal ends of the internal fiber optic cables are supported in the same fiber positioning plate of the previously described embodiment.

In use of the transmission probe, with the probe immersed in the fluid to be tested, electromagnetic radiation is transmitted through one of the fiber optic cables of the probe to the optical window. The transmitted electromagnetic radiation passes through the optical window, through the fluid contained in the fluid testing chamber, and into the retro retroflection assembly. Electromagnetic radiation leaving the retro reflection assembly passes through the fluid in the testing chamber and through the optical window to the other of the fiber optic cables contained in the probe. The optical signal from the probe is transmitted to fluid testing equipment using additional fiber optic cables. The optical signal is used by the test equipment to determine the characteristics and/or properties of the tested fluid.

The third embodiment of the fiber optic fluid probe is called a fluorescence probe. The fluorescence probe makes use of the same tubular body, the spacing and compression tube, the compression ring, and the connector collar of the first described ATR probe embodiment. The fluorescence probe only utilizes a single optical window on the distal end of the probe. Electromagnetic radiation is focused using the optical assembly to a small point a few micrometers from the window surface exciting molecular fluorescence of species present in the process fluid. The same optical assembly used to focus the excitation radiation also collects the fluorescence signal.

The fluorescence probe primarily differs from the previously described probe embodiments in that its optical assembly uses the same components to both focus the exciting electromagnetic radiation and collect the fluorescence signal. The optical assembly is cylindrical and has a hollow interior bore with opposite proximal and distal ends. A spherical lens is contained in the optical assembly bore adjacent the fiber optic cable distal ends. One or more electromagnetic radiation receiving fiber optic cable(s) are positioned at the center of the container bore. The distal ends of these receiving optics are positioned adjacent the center of the spherical lens. A plurality of fiber optic cables is arranged around the receiving fiber optic cable(s). The plurality of transmitting fiber optic cables have distal ends that are positioned adjacent the spherical lens at the periphery of the lens.

The optical assembly is positioned in the interior bore of the tubular body adjacent to the probe body distal end. A resilient seal, preferably an o-ring seal, extends around the optical assembly adjacent its distal end. The resilient seal engages against the tubular probe body at its distal end. The lengths of the fiber optic-cables extend from the optical assembly through the tubular body interior bore to the proximal end of the tubular probe body.

The internal spacing and compression tube is inserted through the interior of the probe body and abuts against the proximal end of the optical assembly. The compression ring is screw-threaded into the probe body proximal end and pushes the spacing tube toward the optical assembly at the probe body distal end. This compresses the resilient seal around the optical assembly, sealing the interior of the probe body.

As in the previously described embodiments, the connector collar is attached to the probe proximal end with the internal fiber optic cables passing through the connector collar. The proximal ends of the internal fiber optic cables are supported in the fiber positioning plate secured in the interior of the connector collar. Secondary fiber optic cables transmit the fluorescence signal from the probe to the fluid processing facility for evaluation.

In use of the fluorescence probe, electromagnetic radiation is transmitted through the transmitting fiber optic cable to the distal end of the optical assembly where the electromagnetic radiation is focused through a spherical lens. The focused electromagnetic radiation excites molecular fluorescence in the fluid at the probe distal end. The fluorescence signal is collected by the spherical lens and transmitted through the receiving fiber optic cable(s) to their proximal end. The fluorescence signal is transmitted from the probe through additional fiber optic cables to the testing equipment. The testing equipment uses the fluorescence signal to determine the characteristics and/or properties of the tested fluid.

BRIEF DESCRIPTION OF THE DRAWINGS

Further features of the invention are set forth in the following detailed description of the preferred embodiments of the invention and in the drawing Figures wherein:

FIG. 1 is a cross-sectional side view of the first embodiment of the fiber optic fluid probe of the invention;

FIG. 2 is a view of several of the unassembled component parts of the mechanical framework of the probe of FIG. 1;

FIG. 5 is an additional view of the probe of FIG. 1, showing a thermocouple and a strain gauge assembled to the probe;

FIGS. 6a and 6b are a cross-sectional side views of a further embodiment of the fiber optic fluid probe;

FIG. 8 is a view of several of the unassembled component parts showing the mechanical framework of the probe of FIG. 6;

FIG. 9 is an enlarged view of the optic crystal of the probe of FIG. 6;

FIG. 10 is an enlarged view of the optic crystal of FIG. 9, rotated 90°;

FIG. 11 is an enlarged view of the optic window of the probe of FIG. 6;

DETAILED DESCRIPTION OF THE PREFERRED EMBODIMENTS

As explained earlier, the present invention provides several different embodiments of fiber optic probes that are employed in various different types of fluid processing facilities. The probes enable testing of fluids (or solids or semi-solid materials present in the fluid) being processed by the facilities without requiring the time delays associated with random sampling of the fluids and without exposing people at the facilities to potentially harmful fluids being tested. Fiber optic probes of this type are known in the prior art. Examples of these types of probes are disclosed in the U.S. Patents of Ponstingel, et al. U.S. Pat. No. 4,637,730; Ponstingel, et al. U.S. Pat. No. 5,241,368; and Masterson, et al. U.S. Pat. No. 6,043,895.

The several embodiments of the fiber optic probes of the invention differ primarily from the probes of the prior art in that the novel constructions of the probes of the invention enable the use of several of the same component parts in the constructions of each of the different probes. The use of the same component parts in the constructions of each of the different probes results in reductions in manufacturing costs due to the reduced inventory of parts required to manufacture the different probe types. The novel constructions of the probes of the invention enable slight modifications to the probes that adapt each probe embodiment for use in a different type of environment and adapt each probe embodiment for use in performing different types of fiber optic testing procedures. Each of the fiber optic probes of the invention is constructed of materials typically employed in constructing such probes, and therefor particular types of materials will not be specified.

The construction of a first embodiment of the fiber optic probe 10 is shown in FIGS. 1-5. This first embodiment of the fiber optic probe 10 senses the affect of a tested fluid on evanescent wave or alternations in the optical sensing element total internal reflection. The probe shown in FIGS. 1-5 is an attenuated total reflectance (ATR) fiber optic probe.

Figure 3:
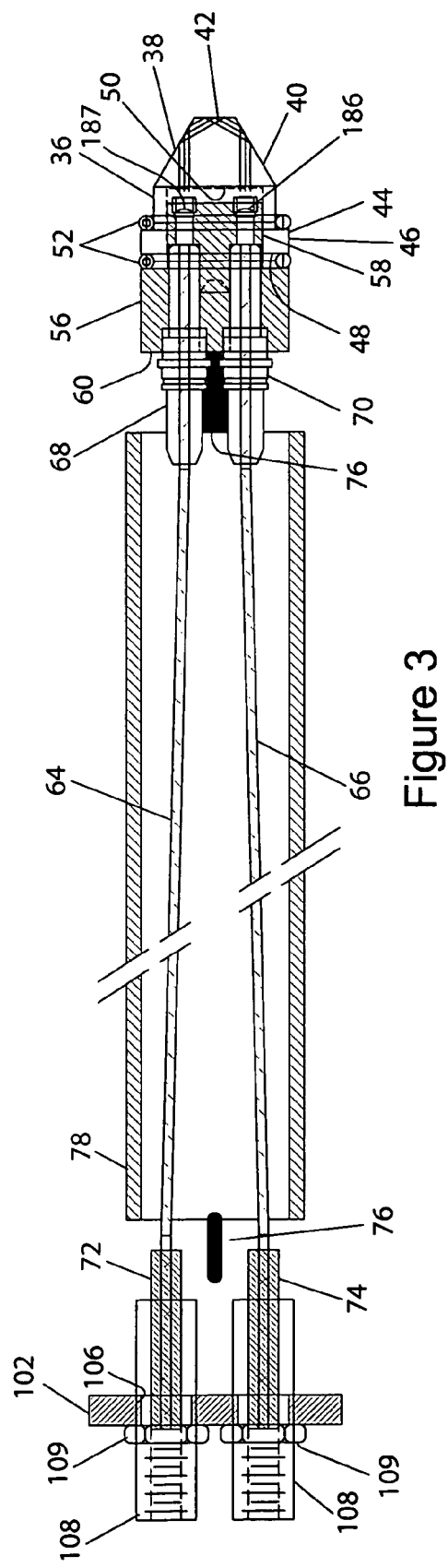
FIG. 3 is a cross-sectional side view of the optic parts of the probe of FIG. 1.

Referring to FIGS. 1-3, the first embodiment of the fiber optic fluid probe 10 is comprised of an elongate tubular body 12. The body 12 is shown fragmented in FIG. 1. It should be understood that the body 12 will have a length that best suits the probe for its intended use. However, in most applications the length of the body 12 will be much longer than that represented by the fragmented probe of FIG. 1. In the preferred embodiment, the probe body 12 has a straight length with opposite proximal 14 and distal 16 ends, a cylindrical exterior surface 18 and a cylindrical interior surface 20. The cylindrical interior surface 20 has a center axis 22 and surrounds a hollow interior bore 24 of the probe. The diameter of the probe body interior bore 24 is consistent along the length of the probe. A majority of the probe body interior surface 20 is smooth, apart from an internally screw-threaded portion 26 of the body interior surface adjacent the body proximal end 14.

A protective tip guard 28 is secured to the body distal end 16. FIG. 2 shows the protective tip guard 28 of FIG. 1, in addition to a second protective tip guard 28' having a slightly different configuration. Each protective tip guard has an annular shoulder 30, 30' that is inserted into the body at the distal end 16. An exterior seem 32 between the protective tip guard 28 and the body exterior surface 18 is welded and then later polished to provide a smooth continuous surface between the body 12 and the protective tip guard 28.

Openings 34, 34' provided in the protective tip guards 28 enable fluid to be tested to flow easily into the interior volumes of the guards.

An optic sensing element 36, for example a sapphire crystal, is positioned at the body distal end inside the protective tip guard 28. The optic sensing crystal 36 has a distal end portion 38 having the shape of a truncated cone or frustum. This gives the crystal distal end portion 38 a conical surface 40 and a flat, circular surface 42. The truncated conical shape of the crystal distal end portion 38 defines three reflecting sensing surfaces of the crystal, which will be explained later. As best seen in FIG. 3, the optic crystal 36 has a cylindrical, "top hat" like shaped proximal end portion 44. An annular collar 46 extends around the crystal proximal end portion 44. The proximal end portion 44 has a flat end surface 48, and a cylindrical cavity 50 is recessed into the flat end surface 48 and into the interior of the optic crystal 36.

A pair of resilient seals 52, in the FIG. 1 embodiment o-ring seals 52, is mounted on the optic crystal proximal end portion 44 on opposite sides of the annular collar 46. With the optic crystal 36 positioned inside the interior bore 24 of the probe body 12, both resilient seals 52 engage and seal against the body interior surface 20. The distal most resilient seal 52 engages against the cap shoulder 30, sealing the body interior bore 24 from the exterior environment of the probe. To further the seal the body interior bore 24, a sealant 54 is applied into the annular groove that surrounds the optic crystal proximal end portion 44 and the interior of the protective cap 28.

There are two versions of the optical insert 56, 56' for use with the probe 10 as seen in FIG. 2. The optical insert 56, 56' is assembled and inserted into the interior bore 24 of the probe body 12 as shown in FIG. 1. As seen in FIG. 2, the optical insert 56, 56' has a cylindrical configuration with a smaller exterior diameter distal end portion 58, 58' and a larger exterior diameter proximal end portion 60, 60'. The distal end portion 58, 58' of the optical insert 56, 56' is cylindrical and is dimensioned to fit in a tight fit in the optic crystal cavity 50. A pair of optical assembly holes 62, 62' extends through the optical insert 56, 56'. As seen in FIG. 2, the distal end portion 58' of the optical insert 56' have two counter bore holes 57 adjacent and on axis to the optical assembly holes 62' for the mounting of lenses 186, 187. The proximal end portion 60, 60' of the optical insert 56, 56' is cylindrical and is dimensioned for a tight sliding fit in the body interior surface 20.

Optical insert 56' has two double step counter bore holes 59 adjacent and on axis to the through holes 62' to aid in mounting of the cylindrical distal ends 68, 70 of the fiber optics 64, 66 and a pair of counter bore holes 63 for mounting of two supporting rods 76 are supplied 90 degrees from the optical assembly holes.

FIGS. 1 and 3 show lengths of fiber optic cables 64, 66 that are assembled into the body interior bore 24. One of the fiber optic cables 64 functions in transmitting electromagnetic radiation through the probe to the probe distal end, and the other of the fiber optic cables 66 functions in receiving reflected electromagnetic radiation, as will be explained. The distal ends of the fiber optic cables 64, 66 are mounted in cylindrical distal sleeves 68, 70 that are positioned in the holes 62, 62' of the assembled optical insert 56, 56'. The distal sleeves 68, 70 securely hold the distal ends of the fiber optic cables 64, 66 against the optic crystal 36 in the crystal cavity 50. The lengths of the fiber optic cables 64, 66 extend through the probe body interior bore 24 to cylindrical proximal sleeves 72, 74 mounted over the proximal ends of the fiber optic cables. FIG. 3 shows one of two supportive rods 76 and a protective thermal sleeve 78 that are packed into the interior bore 24 of the probe body 12 to protect the lengths of the fiber optic cables 64, 66 extending through the interior bore 24 of the probe body 12.

An internal spacing and compression tube 80 is assembled into the interior of the probe body 12. The tube 80 has a cylindrical length with opposite proximal 82 and distal 84 ends. The tube has a cylindrical exterior surface 86 that is dimensioned to fit in a tight but sliding engagement against the probe body interior surface 20. The tube exterior surface 86 is smooth across the entire length of the tube. The tube also has a cylindrical interior surface 88 that is smooth through the entire length of the tube. As seen in FIG. 1, the length of the tube 80 is determined so that the tube distal end 84 will engage with the optical assembly 56 with the tube proximal end 82 positioned in the internally threaded portion 26 of the probe body 12.

A cylindrical compression ring 90 is screw-threaded into the internally screw-threaded portion 26 of the probe body 12 and engages against the spacing and compression tube proximal end 82. Screw threading the compression ring 90 into the probe body interior bore 24 moves the spacing and compression tube 80 toward the distal end of the probe. The movement of the tube 80 compresses the resilient o-ring seals 52 that surround the proximal portion of the optic crystal 36, providing the fluid seal in the interior of the probe body.

A connector collar 92 is attached to the probe body proximal end 14. The connector collar 92 has an externally threaded neck 94 that is screw threaded into the internally screw-threaded portion 26 of the tubular body 12. The connector collar has a hollow interior bore 96 that receives the proximal end sleeves 72, 74 of the fiber optic cables 64, 66, as seen in FIG. 1. The connector interior is provided with an internally screw-threaded portion 98 adjacent a proximal end opening 100 of the connector. The proximal end of the connector collar 92 is provided with an external thread 104 adapted to be attached to conduits (not shown) at a fluid processing facility that protect lengths of additional fiber optic cables that communicate the probe 10 with the testing equipment of the facility.

A fiber positioning plate 102 is mounted in the interior bore of the connector collar 92 as seen in FIG. 1. FIG. 2 shows the fiber positioning plate 102 which is circular and has two internally threaded holes 106 that pass through the plate. FIG. 3 shows the assembly of the positioning plate 102 where the holes 106 receive a pair of mechanical connectors 108 which are adjusted and then fixed with a locknut 109. The connectors 108 receive the proximal sleeves 72, 74 of the fiber optic cables 64, 66. The connectors 108 are known in the art and are employed in providing a electromagnetic radiation transmitting coupling between the fiber optic cables 64, 66 of the probe and the additional fiber optic cables (not shown) of the fluid testing facility.

A connector lock ring 110 is mounted in the interior of the connector collar 92. The lock ring 110 is circular and has external screw-threading 111 at its outer periphery. The ring external screw-threading 111 is screw-threaded into the connector collar internal screw threading 98. The ring 110 is screwed up against the positioning plate 102, thereby locking the positioning plate in its position in the connector collar 92.

In the use of the attenuated total reflectance (ATR) probe 10, the probe is first immersed in a fluid to be tested as is conventional in the use of probes of this type. The probe 10 communicates with a source of electromagnetic radiation at the testing facility, and the electromagnetic radiation is transmitted through the probe transmitting fiber optic cable 64. The electromagnetic radiation is emitted from the transmitting fiber optic cable 64 into the optic sensing crystal 36. As shown in FIG. 1, the electromagnetic radiation is directed by means of a lens 187 from the transmitting fiber optic cable 64 toward a portion of the optic sensing crystal conical surface 40. When two different media with different refractive indices (in this example the optic sensing crystal 36 and the fluid surrounding the optic sensing crystal) contact at an interface (the optic sensing crystal surface), the fluid absorbs some of the electromagnetic radiation energy. In the probe 10 shown in FIG. 1, the electromagnetic radiation transmitted into the optic sensing crystal 36 first reflects off a portion of the crystal conical surface 40, then reflects off the crystal distal end surface 42, and then again reflects off a portion of the optic sensing crystal conical surface 40 before it is reflected back to the receiving lens 186 for focusing into the receiving fiber optic cable 66. The affect of the fluid on absorbing some of the electromagnetic radiation reflected off the optic sensing crystal surfaces is determined by the testing facility. In this way, characteristics and/or properties of the fluid in which the probe 10 is immersed can be determined.

In addition to the above, the probe 10 of FIG. 1 can also be employed in detecting the build up of scale inside a fluid container by detecting the rate of scale build up on the surface of the optic sensing crystal 36. By monitoring the rate of scale build up, a controlled amount of scale inhibitor can be delivered into the fluid processing system to control the scale.

Figure 4:
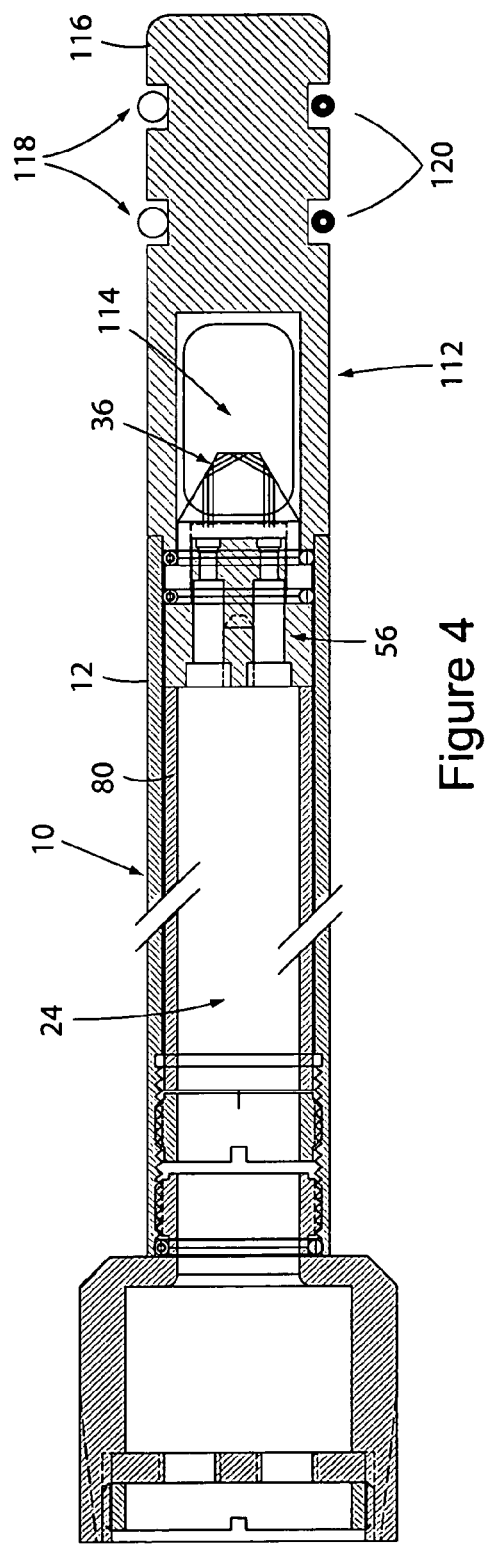
FIG. 4 is a cross-sectional side view of the probe of FIG. 1 employed with a cleaning cap.

FIG. 4 shows the fiber optic probe 10 having a cleaning cap 112 attached to the probe body distal end 16 in lieu of the protective tip guard 28 shown in FIG. 1. The cleaning cap 112 also protects the optic sensing crystal 36. The cap 112 has a pair of diametrically opposed openings 114 that permit the flow of fluid to be tested to enter the cap interior and surround the optic sensing crystal 36. The cleaning cap 112 primarily differs from the previously described protective tip guard 28 in that it is provided with a distal extension 116. A pair of annular grooves 118 is formed in the exterior surface of the extension 116. A pair of resilient seals 120, in the example shown in FIG. 4 o-ring seals 120, is assembled into the pair of annular grooves 118.

Figure 15:
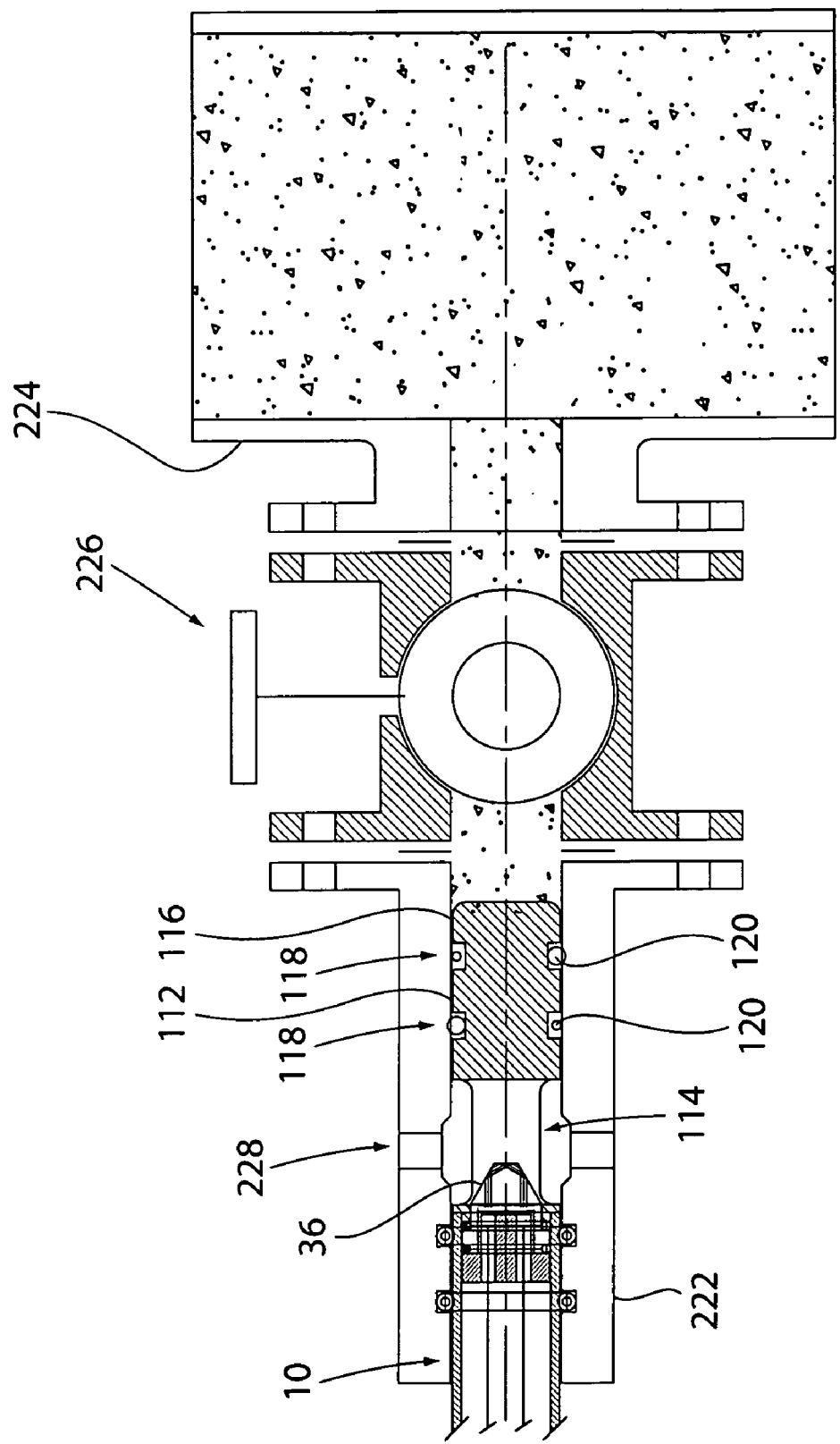
Figure 16:
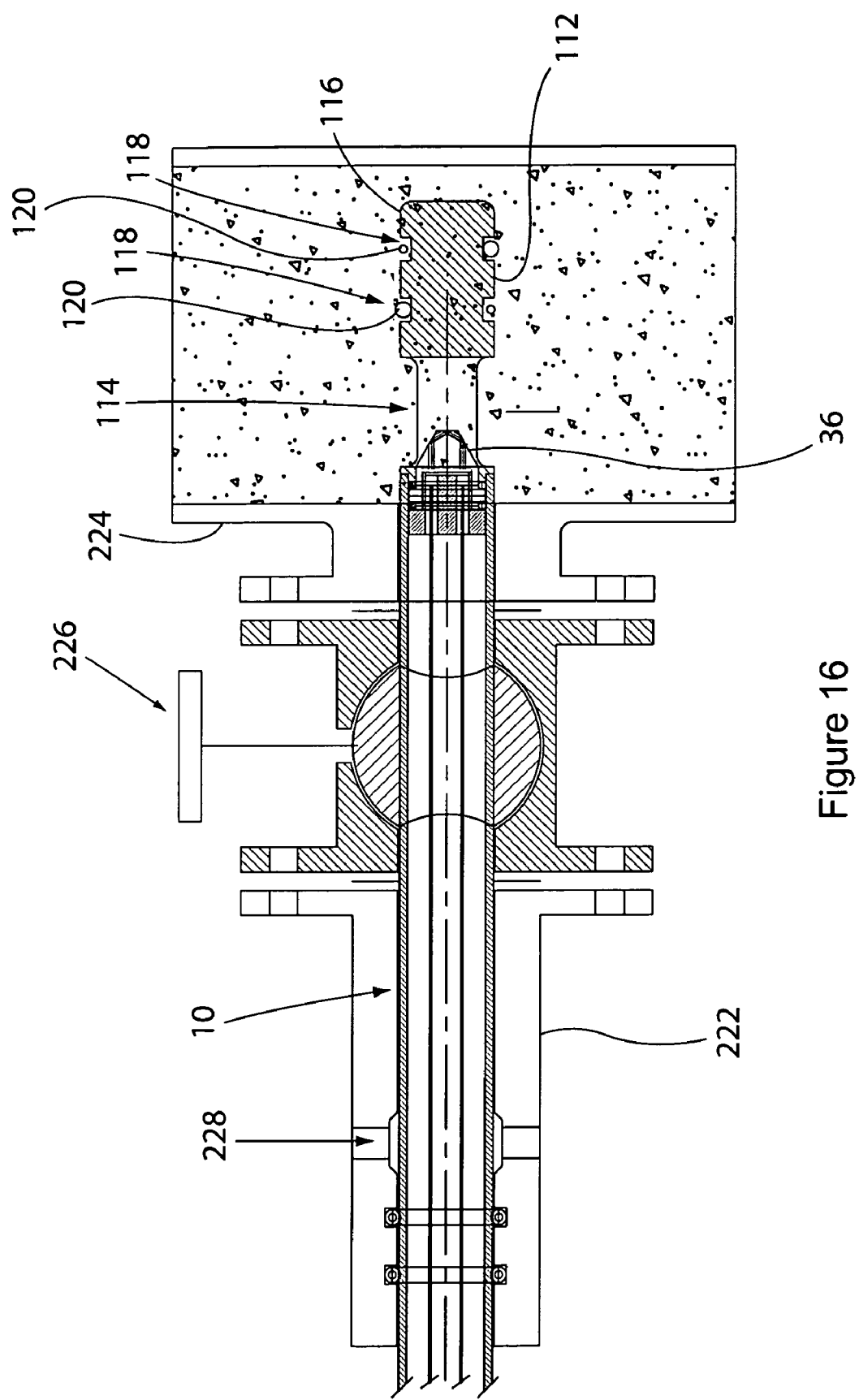

In use of the probe 10 illustrated in FIGS. 15 and 16, the probe is typically inserted through a conduit 222 that intersects with a wall 224 of a container containing the fluid to be tested. The conduit has a valve assembly 226 that is opened to allow passage of the probe through the conduit. The probe 10 is inserted through the conduit 222 and opened valve 226 so that the optic sensing crystal 36 projects into the interior volume of the container containing the fluid.

The cleaning cap 112 enables periodic cleaning of the surfaces of the optic sensing crystal 36. When cleaning is desired, the probe 10 is retracted in the conduit 222 so that the optic sensing crystal 36 is withdrawn out of the interior of the fluid container and into the conduit. The probe 10 is retracted to the extent that the pair of resilient seals 120 on the cleaning cap 112 is also received in the conduit and is positioned on the opposite side of the valve 226 from the container 224. The pair of resilient seals 120 seals the optic probe 10 from the interior of the container containing the fluid being tested. The valve 226 is closed, sealing the probe 10 in the conduit 222. The conduit 222 is provided with a port 228 behind the valve 226 through which cleansing materials can be injected. The cleansing materials are injected into the conduit 222 and enter through the openings 114 of the cleansing cap 112 and surround the exterior surfaces of the optic sensing crystal 36. In this way, the cleansing material cleans the exterior surfaces of the optic sensing crystal 36. When the cleaning operation is completed, the valve 226 is opened and the probe 10 is again extended through the conduit so that the cleaning cap 112 and the optic sensing crystal 36 are again extended into the interior of the fluid container where the exterior surfaces of the optic sensing crystal 36 are again exposed to the fluid being tested.

FIG. 5 shows a further embodiment of the probe 10 of FIG. 1. In the FIG. 5 probe a thermal couple 122 is provided in the optic sensing crystal 36. The thermal couple 122 senses the temperature of the fluid being tested and provides signals through a conductor 124 to the fluid processing facility testing equipment. In addition, the embodiment of the probe 10 shown in FIG. 5 is provided with a strain gauge 126. The strain gauge 126 is positioned just behind the optical assembly 56. The strain gauge 126 is compressed by the pressure of the fluid acting on the optic sensing crystal 36. The compression of the strain gauge 126 produces a signal sent through the strain gauge conductor 128 to the testing equipment of the fluid processing facility, providing a measurement of the fluid pressure.

FIGS. 6-11 show a second embodiment of the fiber optic probe 130 of the invention. The probe shown in FIGS. 6-11 is a transmission probe. One of the beneficial features provided by the novel constructions of the probes of the invention is that each of the different embodiments of the probes, although employed in different methods of testing fluids, makes use of many of the same component parts. Thus, the constructions of each of the probes enables the use of many of the same component parts in each probe which results in a reduction in the costs involved in manufacturing the probes. Because several of the component parts of the transmission probe 130 are the same as those employed in the ATR probe 10, these component parts will not be described in detail. In drawing FIGS. 6-11 the component parts of the transmission probe that are common to those of the ATR probe are identified by the same reference numerals employed in identifying the parts of the ATR probe, with the reference numeral being followed by a prime (').

The transmission probe 130 employs the same tubular body 12', a slightly different optical assembly 56", the same transmitting and receiving fiber optic cables (not shown), the same internal spacing and compression tube 80', the same compression ring 90', the same connector collar 92', the same positioning plate 102', and the same connector lock ring 110' as the ATR probe 10. In the transmission probe 130, the optic sensing crystal 36 of the ATR probe 10 is replaced by a retro reflection assembly 132 that is configured to have two reflective surfaces 134, 136. In addition, an optical window 138 is also assembled into the probe interior. The transmission probe 130 is also provided with a different protective tip guard 140 than that employed on the ATR probe 10.

Figure 6B:
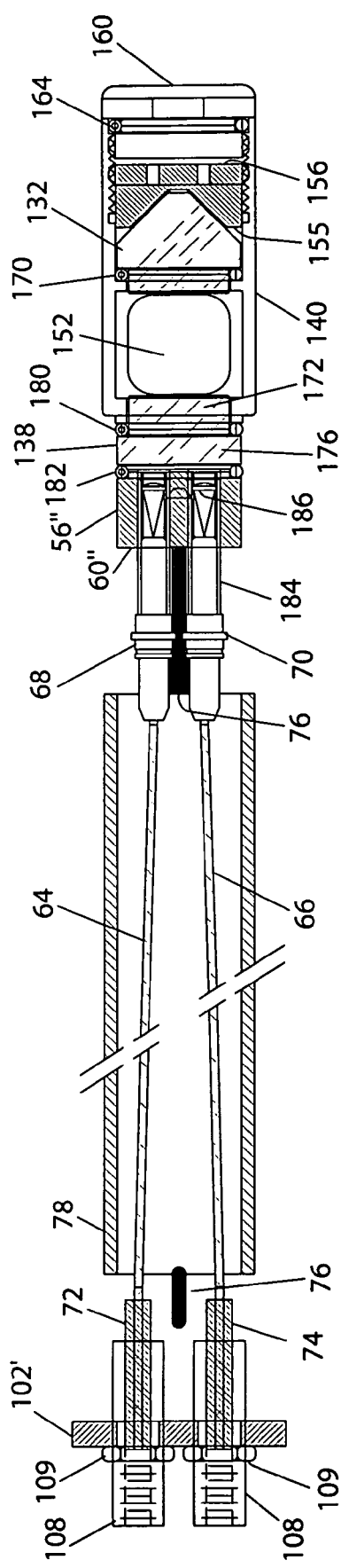
Figure 7:
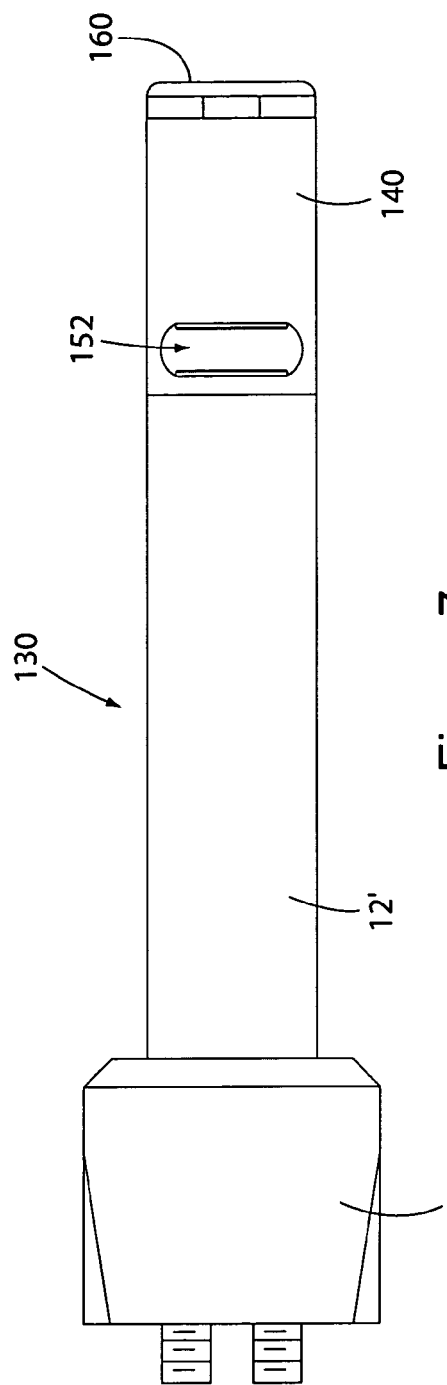
FIG. 7 is a side view of the probe of FIG. 6.

Referring to FIGS. 6-8, the protective tip guard 140 is cylindrical and has a cylindrical interior surface 142 surrounding a hollow interior bore 144 of the guard. The guard 140 extends for a short length between opposite proximal 146 and distal 148 ends of the guard. The guard interior bore 144 extends entirely through the length of the guard between its proximal 146 and distal 148 ends. The interior surface 142 of the guard is provided with internal screw threading 154 adjacent the guard distal end 148. The guard is provided with an annular shoulder 150 at its proximal end 146. The annular shoulder 150 fits into the distal end of the probe tubular body 12'. The guard 140 is secured to the probe tubular body 12' in the same manner as the previously described embodiment. A pair of openings 152 is provided in diametrically opposite sides of the guard.

A positioning plate 156 having an outer periphery with external screw threading 158 is screw threaded into the internal screw threading 154 of the protective tip guard 140. A stopper 160 having external screw threading 162 is also screw threaded into the internal screw threading 154 at the guard distal end 148. The stopper 160 has an annular groove that receives a resilient seal, for example an o-ring seal 164. The resilient seal 164 engages against the interior surface of the protective tip guard 140 with the stopper 160 attached to the guard, sealing closed the guard distal end 148.

The retro reflection assembly 132 is positioned in the interior of the guard 140 with a distal end surface of the assembly abutting against the V-block support disk 155. The V-block disk 155 transfers the sealing pressure evenly to the crystal 132 from the positioning plate 156 as shown in FIG. 6. The retro reflection assembly 132 is shown enlarged in drawing FIGS. 9 and 10. As seen in FIGS. 9 and 10, the assembly 132 has a pair of reflective surfaces 134, 136 that are oriented at an angle relative to each other. The assembly 132 also has a cylindrical proximal portion 166 with a flat, circular end surface 168. A resilient seal, preferably an o-ring seal 170 extends around the assembly proximal portion 166 and engages against the interior surface of the protective tip guard 140 providing a seal between the assembly and the tip guard. As seen in FIG. 6, the positioning of the retro reflection assembly 132 in the interior of the tip guard 140 positions the crystal flat end surface 168 on one side of a hollow interior chamber of the guard as defined between the opposed openings 152 of the cap.

An enlarged view of the optical window 138 removed from the probe is shown in FIG. 11. The window 138 has a "top hat" shape with a cylindrical distal portion 172 with a circular, flat end surface 174. The window has a larger, cylindrical proximal portion 176 with a circular, flat end surface 178. A resilient seal 180, for example an o-ring seal, is positioned around the window distal end portion 172. The seal 180 engages against the protective tip guard annular shoulder 150, sealing the interior bore of the probe body 12' from the test chamber in the guard interior bore 144 between the pair of guard openings 152. An additional resilient seal, for example an o-ring seal 182, is positioned on the opposite side of the window distal end portion 172. This additional seal 182 is compressed by the optical assembly 56", providing an additional seal in the interior of the probe body 12'.

As in the previously described embodiment, the transmission probe 130 could also be provided with a thermal couple for sensing temperature of a fluid, and/or a strain gauge for sensing the pressure of the fluid.

In use of the transmission probe 130, with the probe distal end immersed in the fluid to be tested, electromagnetic radiation is transmitted through the transmitting fiber optic cable 64' to the optical window 138. The electromagnetic radiation passes through the optical window 138 and through the fluid contained in the interior bore testing chamber 144 between the protective tip guard openings 152. The electromagnetic radiation passes through the fluid in the testing chamber and then passes into the retro reflection assembly 132. The electromagnetic radiation reflects off the first surface 134 of the assembly, and then reflects off the second surface 136 of the assembly. The reflected electromagnetic radiation then again passes through the fluid in the testing chamber of the protective tip guard 140. The electromagnetic radiation then passes through the optical window 138 and is received by the receiving fiber optic cable 66'. The electromagnetic radiation is then transmitted by the receiving fiber optic cable 66' to the testing equipment of the fluid processing facility where the optical signal is used to determine the characteristics and/or properties of the tested fluid.

Figure 12:
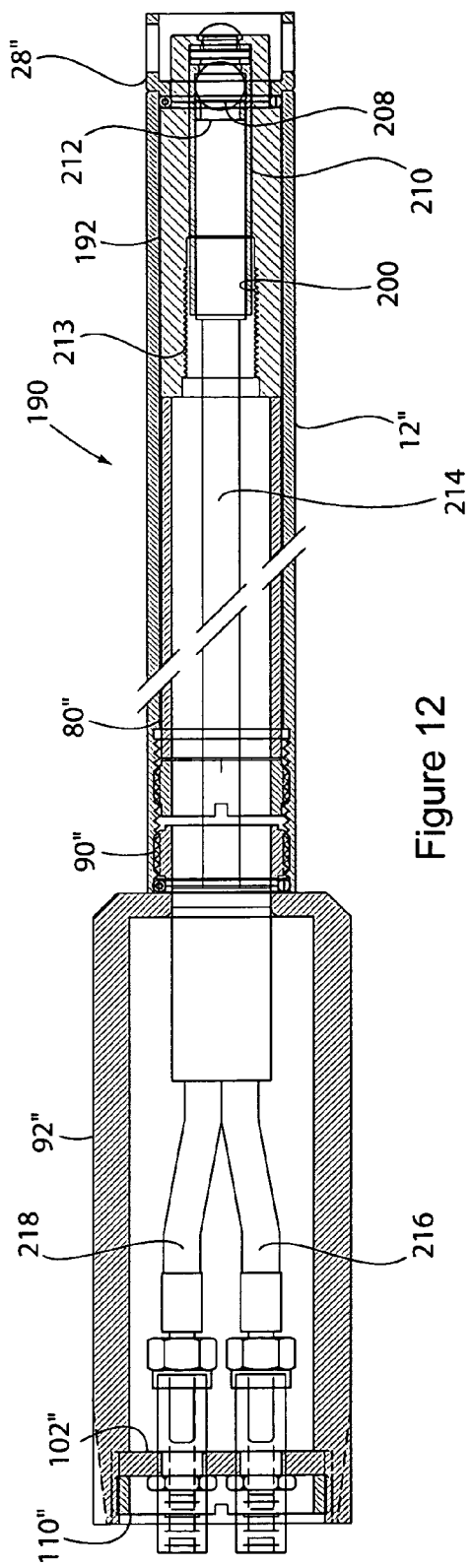
FIG. 12 is a cross-sectional side view of a further embodiment of the fiber optic fluid probe.
Figure 13:
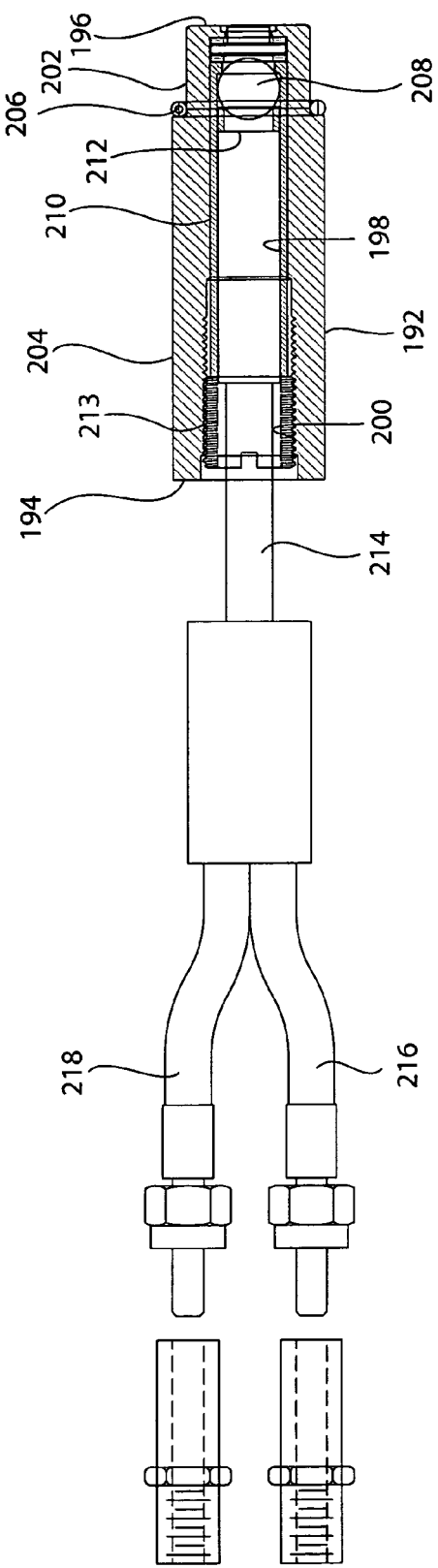
FIG. 13 is a side view of the optic component parts of the probe of FIG. 12 removed from the probe.

FIGS. 12 and 13 show a third embodiment of the fiber optic probe 190. The embodiment of the fiber optic probe 190 shown in FIGS. 12 and 13 is a fluorescence probe. The fluorescence probe 190 makes use of many of the same component parts of the previously described embodiments of the probes, and the same component parts of the ATR probe are identified by the same reference numerals followed by a double prime (").

The fluorescence probe 190 makes use of the same tubular body 12", the same protective tip guards 28, 28' and 28", the same internal spacing and compression tube 80", the same compression ring 90", basically the same connector collar 92" (the connector collar is elongated from those of the previous embodiments), the same positioning plate 102", and the same connector lock ring 110".

The fluorescence probe 190 primarily differs form the previously described embodiments in that it is provided with an optical assembly 192 that uses a plurality of fiber optic cables 214 with a common lens 208 to both focus the exciting electromagnetic radiation and to collect the fluorescence signal. All the fiber optic cables in the assembly can be configured to either transmit or receive electromagnetic radiation. As seen in FIGS. 12 and 13, the optical assembly 192 is cylindrical and has a length with opposite proximal 194 and distal 196 ends. A hollow interior counter bore 198 extends through the length of the optical assembly 192. A portion of the optical assembly interior bore is surrounded by internal screw threading 200 adjacent the assembly proximal end 194. The distal end of the optical assembly 196 has a small opening to expose an optic window 220 to the fluid. A sealant is used to fill the space surrounding the protruding window within the counter bore 188. The assembly exterior surface has opposite distal 202 and proximal 204 end portions. The proximal end portion 204 has a slightly larger exterior diameter dimension than the distal end portion 202. A resilient seal, for example an o-ring seal 206, extends around the optical assembly distal end portion 202. As seen in FIG. 12, the optical assembly 192 is inserted in the interior of the probe body 12" with the resilient seal 206 engaging against the protective tip guard annular shoulder 30, 30', and 30". The spacing and compression tube 80" compresses the resilient seal 206, establishing a seal between the exterior environment of the probe 190 and the interior of the probe body 12".

Figure 14A:
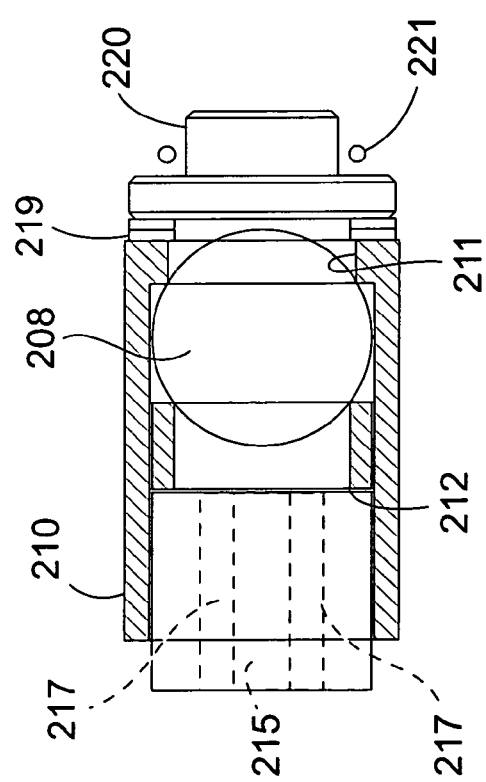
FIGS. 14a and 14b are an enlarged view of a spherical lens of the FIG. 12 probe; and, FIGS. 15 and 16 show the probe of FIG. 4 and an assembly employed to periodically clean the probe.
Figure 14B:
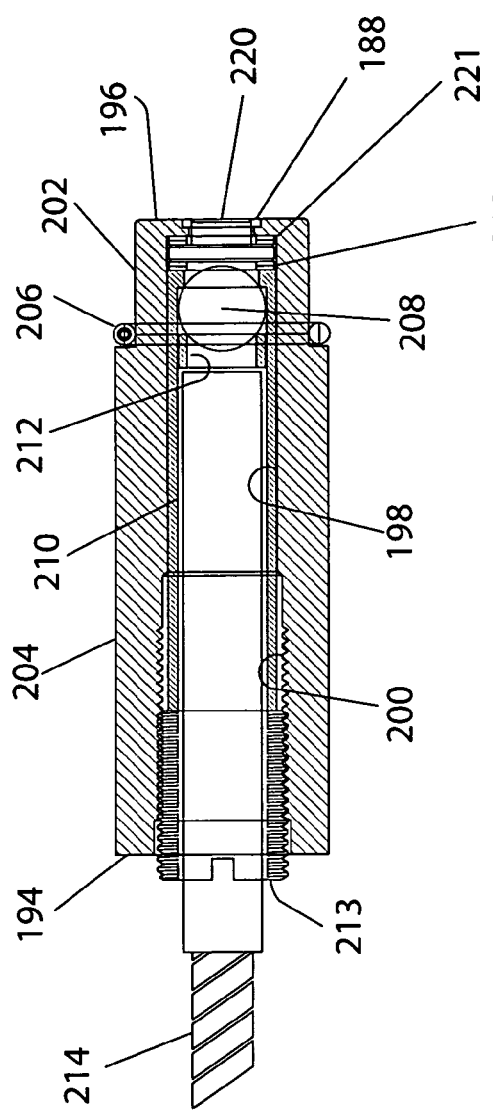

The interior counter bore 198 of the optical assembly 192 contains the fiber optic cluster assembly adjacent to a gasket 219, an optic window 220 and a resilient seal 221 in the distal end 196 of the assembly. For further sealing a sealant may be used to fill the space between the counter bore 188 and the protruding optic window 220. A spacer ring 212 is press fit into the sleeve 210 and holds the lens 208 against the rim 211 as seen in FIG. 14a. In FIG. 12, an externally threaded ring 213 holds the completed sleeve 210 assembly into the proximal end 194 of the optical assembly 192.

The sleeve 210 holds together the distal end of the cluster of fiber optic cables 214 adjacent the center of the spherical lens 208. The electromagnetic radiation receiving fiber optic cable(s) extends through the interior of the probe bore 12" to a proximal end 216 of the fiber optic cable(s) secured in the connector collar 92".

A plurality of electromagnetic radiation transmitting fiber optic cables is arranged around the receiving fiber optic cable(s) of the cluster 214. The transmitting fiber optic cables have distal ends 217 arranged around the receiving fiber optic cable(s) distal end 215. The electromagnetic radiation transmitting fiber optic cables extend through the interior of the probe body 12" to proximal ends 218 of the fiber optic cables positioned in the connector collar 92".

As in the previously described embodiments, the fluorescence probe 190 could also be provided with a thermal couple and/or a strain gauge. In addition, the fluorescence probe 190 could be provided with a cleaning cap for periodic cleaning of the surface of the optic window 220.

In use of the fluorescence probe 190, electromagnetic radiation is transmitted through the transmitting fiber optic cables to the distal ends 217 of the cables where the electromagnetic radiation is transmitted through the spherical lens 208. The transmitted electromagnetic radiation fluoresces in the fluid at the probe distal end. The fluorescence of the electromagnetic radiation is received by the receiving fiber optic cable(s) distal end 215, and the electromagnetic radiation is transmitted though the receiving fiber optic cable(s) to the proximal end 216. The received electromagnetic radiation is transmitted from the probe 190 to the testing equipment of the fluid processing facility. The testing equipment uses the reflected fluorescence electromagnetic radiation to determine the characteristics and/or properties of the tested fluid.

Although the fiber optic probe of the invention has been described above by referring to three specific embodiments of the invention, it should be understood that modifications and variations could be made to the invention without departing from the intended scope of protection provided by the following claims:

What is claimed is:

1. An optic probe comprising:
a tubular body having a hollow interior with a center axis and an axial length with opposite proximal and distal ends, the tubular body having an interior surface with internal screw threading on the tubular body interior surface;
an optical sensing element at the distal end of the tubular body;
a resilient seal between the optical sensing element and the distal end of the tubular body sealing the interior of the tubular body from an exterior environment of the probe, a compression tube inside the tubular body between the tubular body internal screw threading and the optical sensing element, the compression tube having an exterior surface in sliding engagement with the interior surface of the tubular body; and
a compression ring inside the tubular body, the compression ring being screw threaded into the internal screw threading of the tubular body and engaging against the compression tube.

2. The optic probe of claim 1, further comprising:
the seal engaging around a portion of the optical sensing element.

3. The optic probe of claim 1, further comprising:
the tubular body having an interior surface that surrounds the hollow interior and the seal engaging against the interior surface.

4. The optic probe of claim 1, further comprising:
the resilient seal being compressed between the optical sensing element and the tubular body.

5. The optic probe of claim 1, further comprising:
the optical sensing element being a reflective crystal having at least two surface areas that are oriented at an angle to each other.

6. The optic probe of claim 1, further comprising:
at least a portion of the optical sensing element having a conical shape.

7. The optic probe of claim 1, further comprising:
at least a portion of the optical sensing element having a frustum shape.

8. The optic probe of claim 1, further comprising:
a plurality of fiber optic cables extending through the interior of the tubular body, each cable having a proximal end adjacent the tubular body proximal end and an opposite distal end adjacent the tubular body distal end; and
an optical assembly inserted into the tubular body interior adjacent the tubular body distal end, the optical assembly having a plurality of holes extending axially through the optical assembly and the distal ends of the plurality of fiber optic cables being positioned and supported in the plurality of holes.

9. The optic probe of claim 8, further comprising:
a temperature sensor in the tubular body interior.

10. The optic probe of claim 9, further comprising:
the temperature sensor being mounted on and supported by the optical assembly.

11. The optic probe of claim 8, further comprising:
a pressure sensor in the tubular body interior.

12. The optic probe of claim 11, further comprising:
the pressure sensor being mounted in the tubular body interior adjacent the optical assembly.

13. The optic probe of claim 1, further comprising:
the resilient seal being an o-ring.

14. An optic probe comprising:
a tubular body having a hollow interior with a center axis and an axial length with opposite proximal and distal ends,
an optical sensing element at the distal end of the tubular body;
a resilient seal between the optical sensing element and the distal end of the tubular body sealing the interior of the tubular body from an exterior environment of the probe;
a plurality of fiber optic cables extending through the interior of the tubular body, each cable having a proximal end adjacent the tubular body proximal end and an opposite distal end adjacent the tubular body distal end;
an optical assembly inserted into the tubular body interior adjacent the tubular body distal end, the optical assembly having a plurality of holes extending axially through the optical assembly and the distal ends of the plurality of fiber optic cables being positioned and supported in the plurality of holes;
the optical assembly having a first portion with an exterior surface that engages with the tubular body and a second portion that projects axially outwardly from the first portion and is spaced from the tubular body; and
the optical sensing element having an end surface that opposes the optical assembly and a cavity recessed into the optical sensing element from the end surface, and the optical assembly second portion extending into the cavity.

15. The optic probe of claim 14, further comprising:
a resilient seal between the optical sensing element end surface and the optical assembly first portion.

16. An optic probe comprising:
a tubular body having a hollow interior with a center axis and an axial length with opposite proximal and distal ends,
an optical sensing element at the distal end of the tubular body;
a resilient seal between the optical sensing element and the distal end of the tubular body sealing the interior of the tubular body from an exterior environment of the probe;
the distal end of the tubular body being a tubular tip guard secured to the tubular body distal end, with an exterior seam between the tubular tip guard and the tubular body having been welded and later polished providing a continuous, smooth, cylindrical exterior surface between the tubular tip guard and the tubular body.

17. The optic probe of claim 16, further comprising:
the optical sensing element being contained in the tubular tip guard.

18. The optic probe of claim 17, further comprising:
the resilient seal being between the optical sensing element and the tubular tip guard.

19. The optic probe of claim 16, further comprising:
the tubular tip guard having an opening exposing the optical sensing element to the exterior environment of the probe through the tubular tip guard opening.

20. An optic probe comprising:
a tubular body having a hollow interior with a center axis and an axial length with opposite proximal and distal ends,
an optical sensing element at the distal end of the tubular body;
a resilient seal between the optical sensing element and the distal end of the tubular body sealing the interior of the tubular body from an exterior environment of the probe;
a cleaning cap on the tubular body distal end, the cleaning cap extending axially past and enclosing the optical sensing element and having at least one side opening to an interior bore of the cleaning cap; and,
the optical sensing element being inside the cleaning cap interior bore and adjacent the at least one side opening.

21. The optic probe of claim 20, further comprising:
the cleaning cap having an exterior surface; and,
a seal mounted on the cleaning cap exterior surface.

22. An optic probe comprising:
a tubular body having a hollow interior with a center axis and an axial length with opposite proximal and distal ends, the tubular body having an interior surface with internal screw threading;
a plurality of fiber optic cables extending through the interior of the tubular body, each fiber optic cable having a proximal end adjacent the tubular body proximal end and an opposite distal end adjacent the tubular body distal end;
an optical sensing element at the distal end of the tubular body, the optical sensing element having an end surface that opposes the distal ends of the plurality of fiber optic cables and the optical sensing element having a conical surface that is axially opposite the end surfaces;
a compression tube inside the tubular body between the internal screw threading and the optical sensing element, the compression tube engaging in sliding engagement with the tubular body internal surface; and,
a compression ring inside the tubular body and screw threaded into the internal screw threading and engaging against the compression tube.

23. The optic probe of claim 22, further comprising:
the conical surface being on a frustum shaped portion of the optical sensing element.

24. The optic probe of claim 22, further comprising:
an optical assembly inserted into the tubular body interior, the optical assembly having a plurality of holes extending axially through the optical assembly and the distal ends of the plurality of fiber optic cables being positioned and supported in the plurality of holes.

25. The optic probe of claim 24, further comprising:
a temperature sensor in the tubular body interior and supported on the optical assembly.

26. The optic probe of claim 25, further comprising:
a pressure sensor in the tubular body interior.

27. The optic probe of claim 26, further comprising:
the pressure sensor being mounted in the tubular body interior adjacent the optical assembly and the optical assembly being mounted in the tubular body interior for movement of the optical assembly relative to the tubular body and relative to the pressure sensor.

28. An optic probe comprising:
a tubular body having a hollow interior with a center axis and an axial length with opposite proximal and distal ends;
a plurality of fiber optic cables extending through the interior of the tubular body, each fiber optic cable having a proximal end adjacent the tubular body proximal end and an opposite distal end adjacent the tubular body distal end;
an optical sensing element at the distal end of the tubular body, the optical sensing element having an end surface that opposes the distal ends of the plurality of fiber optic cables and the optical sensing element having a conical surface that is axially opposite the end surface;
an optical assembly inserted into the tubular body interior, the optical assembly having a plurality of holes extending axially through the optical assembly and the distal ends of the plurality of fiber optic cables being positioned and supported in the plurality of holes; and,
the optical sensing element end surface having a cavity that is recessed into the end surface and the optical assembly having a portion that extends into the cavity.

29. An optic probe comprising:
a tubular body having a hollow interior with a center axis and an axial length with opposite proximal and distal ends;
a plurality of fiber optic cables extending through the interior of the tubular body, each fiber optic cable having a proximal end adjacent the tubular body proximal end and an opposite distal end adjacent the tubular body distal end;
an optical sensing element at the distal end of the tubular body, the optical sensing element having an end surface that opposes the distal ends of the plurality of fiber optic cables and the optical sensing element having a conical surface that is axially opposite the end surface; and, the distal end of the tubular body being a tubular tip guard secured to the tubular body by a weld that has been later polished, the tubular body and the tip guard thereby having a smooth, cylindrical exterior surface.

30. The optic probe of claim 29, further comprising:

the optical sensing element being contained in the tubular tip guard.

31. The optic probe of claim 30, further comprising:

the tubular tip guard having an opening exposing the optical sensing element to an exterior environment of the probe.

* * * * *